United States Patent [19]

Pearce

[11] Patent Number: 4,785,819

[45] Date of Patent: Nov. 22, 1988

[54] ULTRASONIC IN-LINE SECTOR PROBE

[75] Inventor: Thomas Pearce, Littleton, Colo.

[73] Assignee: Technicare Corporation, Solon, Ohio

[21] Appl. No.: 595,191

[22] Filed: Mar. 30, 1984

[51] Int. Cl.[4] .............................................. A61B 10/00

[52] U.S. Cl. .................................. 128/660.10; 73/634

[58] Field of Search .................... 128/4, 660; 433/118, 433/122; 15/22 R; 350/304, 429; 74/54, 56, 10.6; 73/633, 634

[56] References Cited

U.S. PATENT DOCUMENTS

| | | | |
|---|---|---|---|
| 368,458 | 8/1887 | Clark | 433/122 |
| 410,935 | 9/1889 | Schmidt | 433/122 |
| 3,984,890 | 10/1976 | Collis | 15/22 R |
| 4,130,022 | 12/1978 | Goodrich et al. | 128/660 |
| 4,151,834 | 5/1979 | Sato et al. | 128/660 |
| 4,215,585 | 8/1980 | Kunii et al. | 128/660 |
| 4,282,879 | 8/1981 | Kunii et al. | 128/660 |
| 4,418,698 | 12/1983 | Dory | 128/660 |
| 4,426,886 | 1/1984 | Finsterwald et al. | 73/633 |
| 4,466,444 | 8/1984 | Baba | 128/660 |

*Primary Examiner*—Ruth S. Smith

*Attorney, Agent, or Firm*—W. Brinton Yorks, Jr.

[57] ABSTRACT

A mechanical in-line sector scanner is provided in which the ultrasonic transducer pivots about an axis. The transducer is oscillated through an arc about the axis by reciprocating pins, which alternately push the transducer in opposite directions of scanning. The pins are reciprocated by a continuously turning cam having a cam surface obliquely oriented with respect to the longitudinal axis of the pins.

16 Claims, 2 Drawing Sheets

ULTRASONIC IN-LINE SECTOR PROBE

This invention relates to ultrasonic in-line sector probes for medical ultrasonic diagnostic purposes and, in particular, to such in-line sector probes in which the ultrasonic transducer is physically oscillated to sweep a beam of ultrasound across a target.

In ultrasonic diagnostic imaging, a beam of ultrasound may be swept through tissue in an arc to produce a trapezoidal image of a plane or sector of the tissue. Such sector scanning may be employed to produce highly useful realtime tissue images. In general, there are two methods of sweeping the ultrasonic beam: electronic sector scanning and mechanical sector scanning. In electronic scanning, an array of ultrasonic transducers are excited in predetermined time sequences to develop an ultrasonic wavefront which travels in desired directions. Echoes return from the different directions and through the careful delaying and combining of returning echo information a sector display may be assembled. Electronic scanning is advantageous in that the transducer array will generally have no moving parts. However, this benefit is somewhat offset by the complicated and sophisticated electronics necessary to excite the transducers in the timed sequences, and to delay and process the received echo information.

The opposite tradeoffs are present in the use of mechanical sector scanning. Beam steering is provided by the physical oscillation of the transducer, which may be a simple, single-element crystal. The electronic complexity necessary to process a multitude of returning echo information signals may thereby be reduced or substantially eliminated. This savings in the cost of the electronics is due, of course, to the provision of a mechanical scanning mechanism with a motor, moving parts and the necessity of tracking the instantaneous orientation of the transducer so that the received echo information may be coordinated with the physical location of the echo information sources.

It is thus desirable to use a mechanical scanning technique which is simple, inexpensive, and reliable. Furthermore, the probe with its mechanical oscillation mechanism should be small and easy to handle by a user. A desirable probe of this type is a so-called in-line probe, in which the primary components are oriented in a line along the lengthwise axis of the probe. Such probes are notable for their desirable form factors which facilitate ease of use.

In accordance with the principles of the present invention, an ultrasonic sector scanning probe is provided employing a novel motive means for oscillating the transducer. The piezoelectric transducer is mounted to pivot about an axis. In line with the transducer is a cam swash plate which is rotatably driven and has its cam face oriented toward the transducer. A pair of pins are located between the cam swash plate and the transducer, and are positioned one on either side of the transducer pivot axis. As the cam swash plate turns, the pins move in a reciprocating manner to oscillate the transducer through an arc about its pivot axis. The oscillating mechanism has few moving parts and provides a simple translation of the rotary motion of the cam to oscillation of the transducer. In the drawings:

Figure 3A:
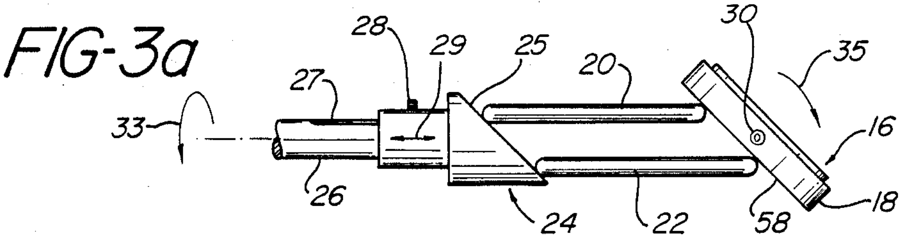
Figure 3B:
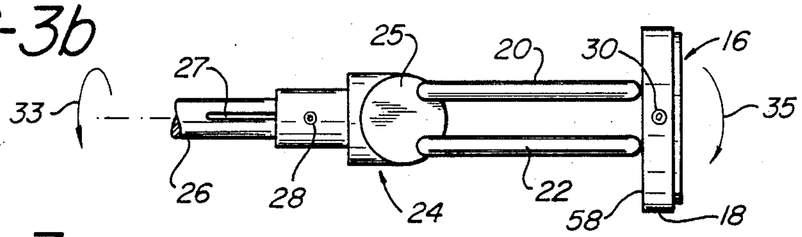
Figure 3C:
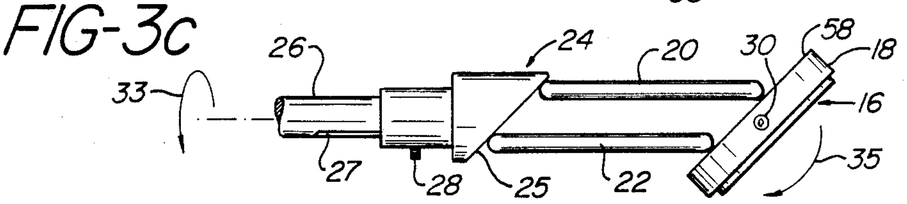
Figure 4:
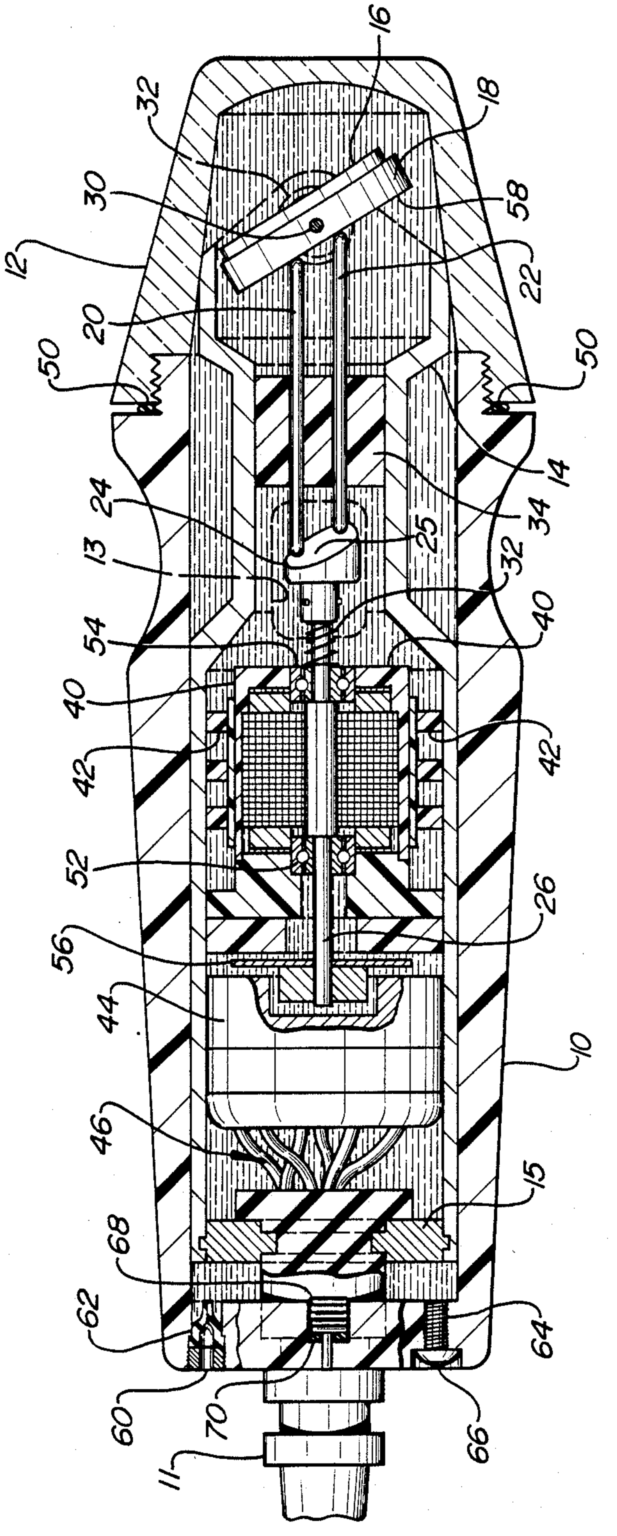

FIGS. 3*a*, 3*b*, and 3*c* illustrate different phases of a cycle of operation of an oscillating mechanism constructed in accordance with the principles of the present invention; and FIG. 4 is a partially cross-sectional view of an in-line ultrasonic probe constructed in accordance with the principles of the present invention.

Figure 1:
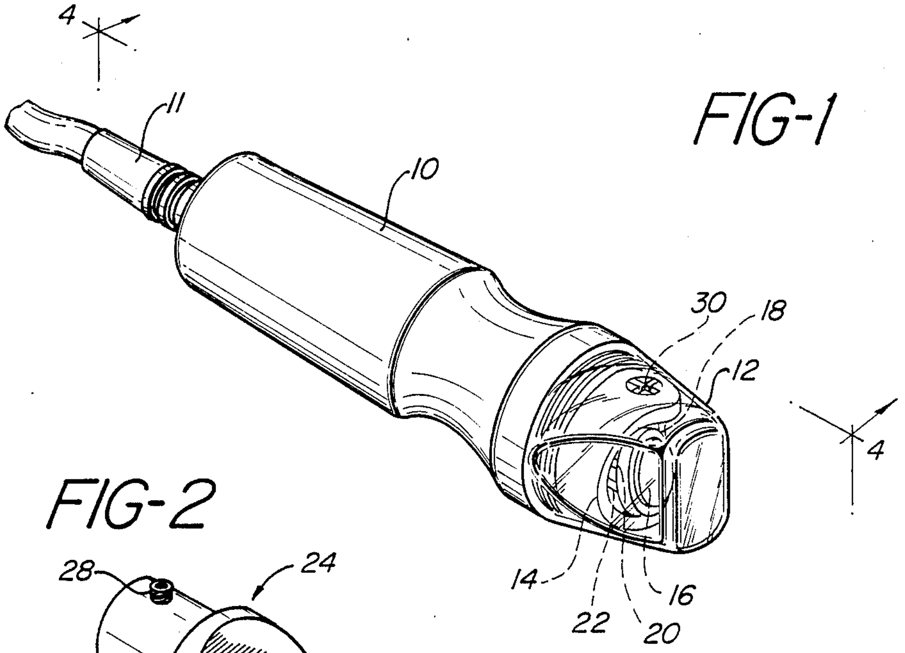
FIG. 1 is a perspective view of an in-line ultrasonic probe constructed in accordance with the principles of the present invention.

Referring to FIG. 1, an in-line ultrasonic probe constructed in accordance with the principles of the present invention is shown. The assembled probe includes a hard plastic case 10, with a transparent or translucent plastic cone 12 mounted at the end to enclose the transducer 16. A cable with a strain relief 11 exits the back of the case. The case is narrowed toward the cone end to allow a user to comfortably grip the probe in the manner of a writing instrument.

The transducer 16 is held in a transducer mounting cup 18. A shaft passes through the mounting cup, with the ends of the shaft riding in bearings in a housing 14. Two reciprocating pins 20 and 22 engage the back of the mounting cup 18.

Figure 2:
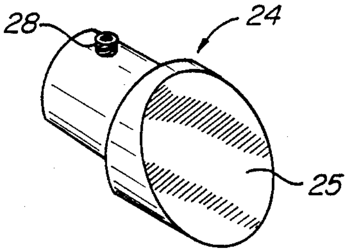
FIG. 2 is a perspective view of a cam swash plate suitable for use in the probe of FIG. 1.

The ends of the pins 20 and 22 remote from the mounting cup 18 engage the cam surface of a cam swash plate 24, which is shown in FIG. 2. The cam swash plate 24 is made of Delrin or other plastic-like material so that the stainless steel pins 20 and 22 will travel smoothly along the cam face 25. At the back of the cam swash plate is a hole suitable for engaging a motor shaft. The operation of the cam swash plate 24 in accordance with the principles of the present invention is illustrated in FIGS. 3*a*, 3*b*, and 3*c*.

In FIG. 3*a*, the cam swash plate 24 is mounted on a motor shaft 26. The motor shaft 26 is axially aligned with the center of the transducer 16 and transducer mounting cup 18. The motor shaft 26 is also aligned with the axis of the transducer shaft 30, about which the transducer pivots. The motor shaft 26 has a groove 27 etched in it, and a set screw 28 in the cam swash plate 24 rides in the groove. The set screw 28 does not clamp the cam swash plate tightly on the shaft, but rather serves to cause the cam to rotate with the motor shaft while allowing the cam to slide on the motor shaft as indicated by arrow 29. As will be seen in the embodiment of FIG. 4, this arrangement permits a spring to constantly urge the cam swash plate to the right and firmly in engagement with the pins 20 and 22. The pins 20 and 22 then contact the back of the mounting cup 18, and are located above and below the axis of the transducer shaft 30.

In the orientation of FIG. 3*a*, the transducer 16 is facing at one extreme of its arc of oscillation. As the motor shaft 26 and cam 24 begin to turn as indicated by arrow 33 (i.e., the top of the shaft 26 begins to move toward the viewer), the transducer 16 and its mounting cup 18 will begin to pivot about shaft 30 as indicated by arrow 35.

After the motor shaft 26 and cam 24 have turned 90°, the components of the oscillation mechanism are located as shown in FIG. 3*b*. To arrive in this orientation, the pins have moved in opposite axial directions as they ride in contact with the cam face 25. The transducer 16 is now at the center of its arc of travel, and is aimed straight out the end of the probe. The plane of the transducer face is normal to the in-line axis of the probe.

As the motor shaft 26 and cam 24 turn further as indicated by arrow 33, the transducer will pivot further as indicated by arrow 35. FIG. 3*c* shows the relative orientation of the components of the oscillation mechanism when the shaft 26 and cam 24 have turned another 90° from their positions of FIG. 3*b*. In FIG. 3*c* the transducer 16 has been pivoted to the extreme of its arc of travel opposite to its starting position of FIG. 3*a*.

When the motor shaft 26 and cam 24 turn further in the direction of arrow 33 from their positions in FIG. 3*c*, the relative axial directions of movement of the pins 20 and 22 will reverse. The transducer 16 will then pivot in the direction opposite to that indicated by arrow 35, and will eventually arrive back in its initial position shown in FIG. 3*a*. Thus, for every 360° of rotation of the motor shaft 26 and cam 24, the transducer will pivot twice through its arc of travel, once in one direction and once in the opposite, returning direction.

The ultrasonic in-line probe of FIG. 1 is shown in detailed partial cross-section in FIG. 4. The arrangement of FIG. 4 makes use of the principle of the oscillation mechanism of FIGS. 3*a*–3*c*. In FIG. 4, the housing 14 is contained within the case 10. The cone 12 is screwed onto the transducer end of the probe, and is sealed with an O-ring seal 50. At the rear of the housing 14 the cable strain relief 11 is seated in an end cap 15. Wires 46 from the transducer 16, a motor 40, and a shaft encoder 44 pass through the probe and into the cable and strain relief 11. The illustrated shaft encoder 44 is an optical position encoder, but other types of encoders, such as a rotary variable differential transformer, may also be employed to encode the rotary position of the motor shaft and hence the angular orientation of the transducer. The motor shaft 26 rides in bearings 52, 54, at opposite ends of the motor 40. The encoding disc 56 of the optical encoder 44 is mounted on the end of the motor shaft 26 entering the encoder, and the cam swash plate 24 is mounted on the forward end of the motor shaft. The forward end of the motor shaft 26 is grooved for the set screw of the cam, and a spring 32 which is under compression is located between the cam 24 and the motor 40. The spring 32 urges the cam 24 against the reciprocating pins 20, 22. The cam, spring and pin mechanism may be viewed through an opening 13 in either side of the housing 14.

In the preceding drawings, the cam face 25 of the cam 24 was shown as a flat surface. However, a flat cam face will cause the oscillatory motion of the transducer to vary sinusoidally in velocity. In FIG. 4, the cam face 25 is not flat, but is a curved sinusoidal surface. The sinusoidal surface causes the transducer to oscillate with a more constant linear velocity than the flat surface, and thereby allows the subject to be more evenly insonified. Ease of image reconstruction is also afforded by the linear oscillation of the transducer. It may be noted that the back surface 58 of the transducer mounting cup 18 is also effectively a cam surface on which the reciprocating pins 20, 22 ride. This surface 58 may also or alternatively be a shaped cam surface if desired. Furthermore, the angle of the cammed surfaces determines the angle of the scanning arc of the transducer. When the back surface 58 of the mounting cup is flat, a 45° angle of the cam face will provide a 90° scanning arc. Similarly, a 30° cam face angle will provide a 60° scanning arc.

The reciprocating pins 20, 22 are retained in position by a pin guide 34. Lubrication of the pins in the guide 34 is provided by the ultrasonic fluid located throughout the probe.

The transducer mounting cup 18 holds the transducer 16. The cup 18 is mounted on a hollow shaft 30, which passes through opposite sides of the cup. The ends of the shaft are mounted in bearings, one of which, bearing 32, is shown in the FIGURE. The coaxial wires which conduct signals to and from the transducer enter holes in the shaft inside the cup 18, and pass through the hollow shaft 30 and out the bearing-mounted ends of the shaft, and the housing. The transducer wires then extend back through the probe and into the cable and strain relief 11. When a multielement transducer such as an annular array is used in the probe, the wires may be twisted several times as they enter and pass through the hollow shaft 30. The transducer wires will then slightly untwist and retwist as the transducer oscillates.

The probe is pressurized with ultrasonic fluid which is contained throughout the probe in a manner not relevant to the claimed invention. Parts associated with the filling mechanism include a fill port 64, a check valve 62, a seal screw 66, a valve hole plug 60, an expansion bellows 68, and a bellows seal 70, all being well-known in the art. [Initial filling of the probe is done through a fill port 64. While the probe is being filled, a check valve 62 is removed from the back of the probe, and the aperture vacated by the valve 62 is used as a vent port. The valve 62 is then replaced. After the probe has been filled with fluid, the fill port 64 is plugged with a seal screw 66. The ultrasonic fluid is then injected into the assembled probe through a duck-billed check valve 62 located in the rear of the case 10, next to the strain relief cable 11. The check valve 62 is accessed through a hole in the case, which is normally plugged by a valve hole plug 60. The vent hold is left open initially during fluid injection to purge any remaining air bubbles from the probe. Thereafter, the vent hole is plugged and the probe is pressurized to the desired fluid pressure. Pressurization causes an expansion bellows 68 to compress. The expansion bellows 68 is seated on a bellows seal 70. Should any fluid leakage occur with time, the compressed bellows will expand slightly to maintain the fluid pressure within the probe. Expansion of the bellows to maintain fluid pressure extends the time period between injection pressurizations.]The ultrasonic fluid completely fills the probe so that the moving parts ride in a fluid bath and so that ultrasonic wave transmission and echo reception is done through the fluid in front of the transducer 16.

The in-line probe of FIG. 4 is seen to be relatively compact in configuration, with a short acoustic beam path between the transducer 16 and the cone 12 to reduce attenuation of the beam before it enters the patient's body. Beam penetration is thereby improved, which allows tissue to be imaged at relatively sizeable depths within the body. The motor 40 continuously turns in one direction, which permits the use of a relatively low power, simple motor. There is no vibration from accelerating and decelerating rotational inertias, which is the case in various other oscillating mechanisms where the direction of oscillation is reversed by mechanically reversing the drive mechanism. Only the transducer and its mounting cup reverse direction in a turbulent manner in the probe, which is the minimal requirement in a mechanical probe. This keeps bubble generation in the ultrasonic fluid to a minimum, and also reduces the possibility of reverberation artifacts. Furthermore, the fluid bath throughout the probe eliminates dynamic fluid seals around moving parts everywhere but at the motor shaft bearings. Finally, the probe may alternately be provided with one or two types of cones; a hard plastic cone for scanning through intercostal and parasternal spaces, and a soft plastic cone for neonatal head scans.

What is claimed is:

1. In an ultrasonic transducer probe for mechanical sector scanning, apparatus for oscillating a transducer comprising:

an ultrasonic transducer having a front ultrasonic energy transmitting surface and an opposing back surface, and mounted for oscillation about a first axis;

a cam, mounted for rotation about a second axis normal to said first axis, said cam having a cam surface opposing said back surface of said transducer which cam surface is obliquely oriented with respect to the the plane of said first axis which is normal to said second axis; and a pair of pins, located between said cam surface and said back surface of said transducer, and driven by said cam in a reciprocating manner so as to oscillate said transducer about said first axis.

2. The ultrasonic transducer probe of claim 1, wherein said pins are oriented along respective third and fourth axes which are parallel to said second axis.

3. The ultrasonic transducer probe of claim 1, wherein said pins oppose said back surface of said transducer on respective opposite sides of said first axis.

4. The ultrasonic transducer probe of claim 3, further including a motor having a motor shaft for rotating said cam, said cam being mounted on said motor shaft, and said motor shaft being aligned with said second axis.

5. The ultrasonic transducer probe of claim 4, further including a transducer mount for retaining said transducer, said transducer mount including a shaft aligned with said first axis, wherein said pins contact a surface of said transducer mount remote from said transducer.

6. The ultrasonic transducer probe of claim 4, wherein said cam is mounted on said motor shaft so as to rotate with said shaft and is movably mounted for sliding on said motor shaft along said second axis.

7. The ultrasonic transducer probe of claim 1, further including means for detecting the angular position of said transducer during oscillation about said first axis.

8. The ultrasonic transducer probe of claim 7, wherein said cam surface is substantially flat.

9. The ultrasonic transducer probe of claim 7, wherein said cam surface is curved.

10. An ultrasonic transducer probe for mechanical sector scanning comprising:

a hollow case having a longitudinal axis;

an ultrasonic transducer pivotally mounted in said case for oscillation about an axis which is normal to said longitudinal axis;

a motor mounted within said case and having a motor shaft aligned along said longitudinal axis;

a cam mounted on said motor shaft and having a cam surface opposing said transducer, said cam surface being obliquely oriented with respect to said longitudinal axis; and a pair of reciprocating pins, located between said cam surface and said transducer on opposite sides of said pivot axis of said transducer.

11. The ultrasonic transducer probe of claim 10, further including a pin guide means located between said cam and said transducer for maintaining said location of said pins on said opposite sides of said pivot axis of said transducer.

12. The ultrasonic transducer probe of claim 11, further including means, connected to said motor shaft, for providing signals indicative of the position of said transducer in its arc of sector scanning.

13. The ultrasonic transducer probe of claim 12, further including a compression spring means, located between said motor and said cam, for urging said cam surface toward said pins.

14. The ultrasonic transducer probe of claim 13, wherein said motor shaft is grooved, and wherein said cam includes a projection means projecting into said groove for causing said cam to rotate with said motor shaft.

15. The ultrasonic transducer probe of claim 10, wherein said ultrasonic transducer is mounted on a pivoting hollow shaft, and wherein said transducer includes a signal lead extending through said hollow shaft.

16. The ultrasonic transducer probe of claim 10, wherein said hollow case is pressurized with ultrasonic fluid, ultrasonic energy passing through said fluid before leaving said case.

* * * * *